United States Patent [19]

Kao

[11] Patent Number: 4,565,879

[45] Date of Patent: Jan. 21, 1986

[54] PROCESS FOR PRODUCING SUBSTITUTED PYRROLES

[75] Inventor: James T. F. Kao, Baton Rouge, La.

[73] Assignee: Ethyl Corporation, Richmond, Va.

[21] Appl. No.: 137,250

[22] Filed: Apr. 4, 1980

[51] Int. Cl.$^4$ ........................................... C07D 207/34
[52] U.S. Cl. .................................................. 548/531
[58] Field of Search .................... 260/326.46; 548/531

[56] References Cited

U.S. PATENT DOCUMENTS

| 3,752,826 | 8/1973 | Carson | 260/326.46 |
|---|---|---|---|
| 3,865,840 | 2/1975 | Carson | 260/326.46 |
| 3,952,012 | 4/1976 | Carson | 260/326.46 |
| 4,048,191 | 9/1977 | Carson | 260/326.46 |
| 4,374,255 | 2/1983 | Kao et al. | 548/531 |

FOREIGN PATENT DOCUMENTS 2942140  4/1980  Fed. Rep. of Germany.

*Primary Examiner*—Alton D. Rollins
*Attorney, Agent, or Firm*—Donald L. Johnson; John F. Sieberth

[57] ABSTRACT

A process for the preparation of alkyl 1,4-dimethyl-3-ethoxycarbonylpyrrole-2-acetate compounds by reacting a diloweralkyl acetone dicarboxylate, a chloromethyl lower alkyl ketone and an aqueous loweralkylamine in the presence of an added organic hydrocarbyl aromatic compound as co-solvent.

4 Claims, No Drawings

PROCESS FOR PRODUCING SUBSTITUTED PYRROLES

BACKGROUND OF THE INVENTION

This invention relates to a process for producing substituted pyrroles, especially pyrrole-2-acetic acids and derivative compounds thereof. More particularly, the process of this invention is concerned with processes which produce a 1,4-diloweralkyl-3-loweralkoxycarbonyl-pyrrole-2-acetate which is a useful intermediate for analgesic and anti-inflammatory pharmaceutical compounds.

It has been found difficult in the past to substitute pyrrole rings, which already contain substituents at other positions on the ring, at the 4-position because of steric hindrance and ring deactivation. Thus, Carson, U.S. Pat. No. 3,752,826 and U.S. Pat. No. 3,865,840, teach the preparation of certain 4-substituted 5-aroyl-pyrrole alkanoic acids and the corresponding salts, esters, nitriles, amides and substituted amides thereof represented by the formulas:

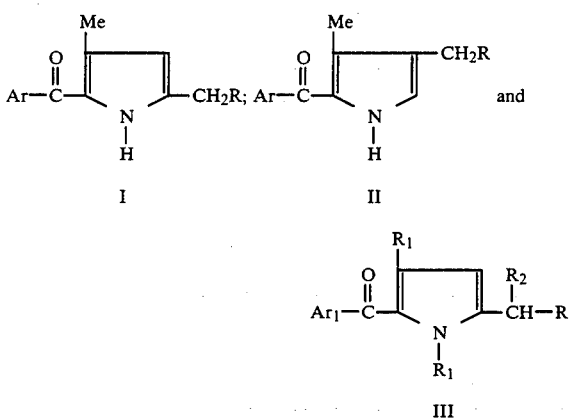

wherein:
Ar represents a member selected from the group consisting of phenyl, monosubstituted phenyl and polysubstituted phenyl, each substituent of said substituted phenyls being a member selected from the group consisting of halo, lower alkyl and lower alkoxy;
$Ar_1$ represents a member selected from the group consisting of phenyl, thienyl, 5-methylthienyl, monosubstituted phenyl and polysubstituted phenyl, each substituent of said substituted phenyls being a member selected from the group consisting of halo, lower alkyl, trifluoromethyl, lower alkoxy, nitro, amino, cyano, and methylthio;
R represents a member selected from the group consisting of COOH, COO-(lower alkyl), $CONH_2$, CONH-(lower alkyl) and CON-(lower alkyl)$_2$;
$R_1$ represents lower alkyl;
$R_2$ represents a member selected from the group consisting of hydrogen and lower alkyl, provided that when said Ar is a member of the group consisting of nitrosubstituted phenyl, then, with regard to Formula III, $R_2$ is hydrogen;
Me is methyl;
and the non-toxic, therapeutically acceptable salts of such acids, such as are obtained from the appropriate organic and inorganic bases. According to Carson, supra, the 4-substituted 5-aroylpyrrole alkanoic acids must be obtained by condensation of the appropriate 1-aryl-1,2,3-butanetrione-2-oxime and an appropriate dialkyl acetonedicarboxylate as starting materials to provide the corresponding ring-closed pyrrole, alkyl 5-aroyl-3-alkoxy- carbonyl-4-methylpyrrole-2-acetate; or by condensation of an appropriate chloromethyl lower alkyl ketone added to a mixture of an appropriate di-lower alkyl acetonedicarboxylate, preferably the diethyl ester and a loweralkyl amine to provide the ring-closed pyrrole, alkyl 1,4-diloweralkyl-3-alkoxycarbonyl pyrrole-2-acetate. These pyrrole intermediates are then treated as disclosed in U.S. Pat. No. 3,752,826 and 3,865,840 to obtain the desired 5-aroyl-4-lower alkyl-pyrrole-2-alkanoic acids and acid derivatives thereof useful as anti-inflammatory agents.

The condensation of chloromethylketone, ammonia and hydroxy crotonic acid alkylester through aminocrotonic acid ester is taught by Fischer and Orth, *Die Chemie Des Pyrroles*, pp. 5–6 and 233–234, Edward Brothers, Inc., Ann Arbor, Mich., 1943. However, neither the 4-alkyl-substituent nor the diester functionality is disclosed in this reference.

Another pyrrole ring-closure synthesis, known as the Hantzsch pyrrole synthesis, teaches the interaction of alphachloro-aldehydes or ketones with beta-ketoesters and ammonia or amines to give pyrroles, Gowan and Wheeler, *Name Index of Organic Reactions*, p. 116, Longmans, Green and Co., Ltd., New York, N.Y., 1960.

In a similar manner, there is taught the reaction of chloroacetone with a salt produced from reaction of methyl amine and diethyl acetone dicarboxylate to give a 4-methylpyrrole, Jones and Bean, *The Chemistry of Pyrroles*, p. 59, 104, Academic Press Inc., New York, 1977. Also, the pyrrole synthesis from chloromethyl ketones and beta-ketocarboxylic esters with ammonia or amines is known, Krauch and Kunz, *Organic Name Reactions*, p. 211, John Wiley and Sons, Inc., New York, 1964. However, such teachings either fail to suggest the possibility of the pyrrole diester compounds or teach no more than Carson, supra, and are based thereon.

Specifically pertinent to the improved process of this invention, U.S. Pat. No. 3,752,826 and 3,865,840 teach that after reaction of, for example, aqueous methylamine with diethyl acetone-dicarboxylate and then adding chloroacetone at a temperature below 60° C. for a period of two hours, the resultant reaction mixture is poured into ice-hydrochloric acid. The acidification acts to dehydrate the intermediate dihydroxy pyrrolidine to the desired pyrrole. However, the reaction forms solid intermediates which are difficult to agitate and conversion of the intermediate to the desired product results in an exothermic reaction which is difficult to control on a large scale. Accordingly, the reaction could be improved to control the formation of solids and moderate the exothermic reaction.

THE INVENTION

In a search for improved processes for the reaction of a loweralkyl amine in aqueous solution with a diloweralkyl acetone dicarboxylate, it was discovered that the reaction occurs in the organic phase not in the aqueous phase. Therefore, it was hypothesized that a reaction medium having the ability or characteristic of lower solubility for the amine than for the diloweralkyl acetone dicarboxylate would limit the rate of reaction and hence, lower the heat load as well as provide solubility for the intermediate product. While not wishing to limit the present and improved process to any theory or mechanism of reaction, it has been found that certain organic solvents have the necessary characteristics required to provide the improved process. Accordingly, the present invention provides a process for the preparation of a loweralkyl 1,4-dilower-alkyl-3-loweralkoxycarbonyl-pyrrole-2-acetate of the formula:

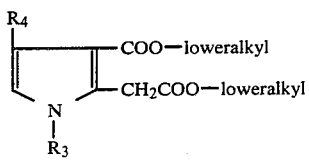

by reacting a mixture of a chloromethyl loweralkyl ketone of the formula: $Cl-CH_2-CO-R_4$, with a diloweralkyl acetone dicarboxylate of the formula:

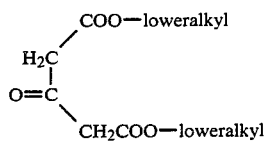

and an aqueous solution of a loweralkylamine of the formula: $R_3NH_2$, wherein the foregoing formulas said $R_3$ and said $R_4$ represent loweralkyl, the improvement comprising said reacting being carried out in the presence of an added co-solvent in which said diloweralkyl acetone dicarboxylate is soluble and which can extract said loweralkylamine from the aqueous phase at a rate so that the exothermic reaction is moderated and the product remains in solution.

As used in this invention, "loweralkyl" and "loweralkoxy" may be straight or branch chained saturated hydrocarbons having from 1 to 6 carbon atoms, such as, for example, methyl, ethyl, propyl, isobutyl, isopropyl, butyl, pentyl, hexyl and the like alkyls and, respectively, the corresponding alkoxys such as methoxy, ethoxy, propoxy, isopropoxy, and the like.

The loweralkyl 1,4-diloweralkyl-3-loweralkoxycarbonyl-pyrrole-2-acetate of the present invention is preferably produced when the chloromethyl loweralkyl ketone is a chloroacetone. Chloroacetone is a readily available and relatively inexpensive ketone. The dicarboxylate is preferably dimethyl or diethyl acetone dicarboxylate which can be prepared according to known procedures. The other reactant is a loweralkylamine, preferably methylamine in order to have a 1-methylpyrrole compound produced. Should other 1-substituted pyrroles be desired, then other amines such as aryl amines or other alkyl amines, are also suitable reactants in the process of this invention. However, preferably, in order to produce the 1,4-diloweralkyl pyrrole compound, methylamine is used. Preferably, a 40% solution of methylamine is employed since this is conveniently available. More preferably, the solution is a 40% aqueous solution of methylamine.

The added co-solvent employed in the process of this invention is an organic solvent with a high degree of solubility for the dialkyl acetone dicarboxylate and the cyclized, substituted pyrrole product. Additionally, the added co-solvent must be relatively water-immiscible and capable of extracting the loweralkylamine from the aqueous solution thereof for reaction in the organic phase.

It has been found that several types of organic solvents have utility in the present process. Typically, organic solvents which are aromatic hydrocarbon compounds and have boiling points from about 75° to about 150° C. at normal pressures are particularly suitable because such solvents in addition to preventing solids formation by solubilizing reactants and products also provide a method of convenient heat removal by operation at reflux. Specifically, simple aromatic hydrocarbons, such as benzene, xylene and toluene are useful and practical added co-solvents in the process of the present invention. Of particular preference, toluene provides the combined properties of solubility, heat removal, water-immiscibility, sufficient inertness to the reactants and products and low cost for best results in the present process. Although toluene is preferred, any aromatic hydrocarbon solvent having similarly advantageous properties can be used. It is only necessary to maintain the diloweralkyl acetone dicarboxylate and the substituted pyrrole in solution while extracting the lower alkyl amine from aqueous solution to be usefully employed in the present process.

In addition to dissolving the product alkyl 1,4-dimethyl-3-ethoxycarbonylpyrryl-2-acetate, aromatic hydrocarbon added co-solvents also reject impurities such as uncyclized intermediates and ionic species. Further, the densities of the aromatic hydrocarbon solvents are lighter than water so that in commercial scale equipment the added co-solvent is found as the upper layer upon phase settling and the aqueous lower layer containing unreacted materials and impurities can be simply drained off. Thus, the use of an aromatic hydrocarbon as an added co-solvent achieves a minor mid-process purification and separation objective when the substituted pyrroles produced are carried on to the preparation of analgesic and antiinflammatory pharmaceutical compounds.

The reaction of, for example, diethyl acetone dicarboxylate, methylamine and chloroacetone is carried out by adding an aqueous solution of methylamine to a solution of the other reactants in, for example, methylene chloride. Although not preferred, the addition may also be carried out inversely, i.e., adding a solution of diethylacetone dicarboxylate and chloroacetone to a solution of aqueous methylamine. Temperatures, depending upon the nature of the added co-solvent employed will range initially from about 25° C. up to the reflux temperature of the solvent. The reaction is conducted for a period of time sufficient to complete the reaction and then the resultant solution is acidified or thermally cyclized to finish the product.

The process of the present invention can be illustrated, but not limited, more fully by the following Examples.

EXAMPLE 1

To a suitable reaction flask were charged 100 grams of 40% aqueous methylamine. The flask was cooled to 5° C. Then a mixture of 60 grams toluene, 30 grams diethyl acetone dicarboxylate and 28 grams chloroacetone was mixed and rapidly fed in about 13 minutes to the reaction flask while keeping the temperature of the reaction mixture at 15° C. The temperature increased to 25° C. Thereafter, the reaction mixture was stirred for about one hour at 25° C. Then the reaction mixture was cooled to 5° C. and 133 grams of concentrated (37%) hydrochloric acid was added, stirred for 5 minutes and layers were separated.

Analysis of the organic layer indicated 38.1 percent yield of the desired ethyl 1,4-dimethyl-3-ethoxycarbonylpyrryl-2acetate having about 90% purity after evaporation of toluene solvent.

EXAMPLE 2

To a suitable reaction flask were added 100 grams of 40% aqueous methylamine and it was cooled to 5° C. Then was added a mixture of 30 grams of diethyl acetone dicarboxylate and 60 grams of toluene while keeping the temperature at 15° C. Immediately thereafter 28 grams of chloroacetone were added. During addition, the temperature rose briefly to 43.7° C. However, the reaction mixture was cooled to 25° C. and maintained at that temperature with stirring for 1 hour. Then, after adding an additional 50 grams of toluene, 133 grams of concentrated (37%) hydrochloric acid were added to the reaction flask while maintaining the temperature at 5° C. The reaction mixture was stirred for about 5 minutes and after settling the organic and aqueous phases were separated.

The organic phase was heated on a Rotovap laboratory evaporator to dryness and oven vacuum dried overnight. Analysis of the organic phase indicates 53.7 percent yield of ethyl 1,4-dimethyl-3-ethoxycarbonylpyrryl-2-acetate. The weight of dry solids indicates a yield of 52.4 percent yield with 89.6 percent purity of the product.

EXAMPLE 3

To a suitable reactor were charged 333 grams of toluene. Thereto were added 76 grams of diethyl acetone dicarboxylate and 70 grams of chloroacetone. The mixture was cooled to 25° C. and 256 grams of 40% aqueous methylamine were fed to the reaction mixture over a period of 0.5 hours. The temperature was maintained at 39°–40° C. during addition and the agitation continued over an additional 0.5 hour period after cessation of the methylamine feed.

After cooling to 15° C., 340 grams of concentrated (37%) hydrochloric acid were added to the reaction mixture as rapidly as possible while maintaining the temperature at 15° C. The organic and aqueous phases were then separated. The toluene was removed from the organic phase by evaporation at 50° to 80° C. giving a melt of product ethyl 1,4-dimethyl-3-ethoxy- carbonylpyrryl-2-acetate, which analyzed by VPC as a 57.2 percent yield.

EXAMPLE 4

To an ice water cooled solution of 50 ml of 40 weight percent aqueous methylamine was added a solution of 13.3 grams of diethylacetone carboxylate in 40 ml of toluene over a period of about one minute. Then 11.9 grams of chloroacetone were added. The exothermic reaction increased the reaction mixture temperature from 22° to 42° C. The reaction was stirred for 1 hour at ambient temperature then heated to 80° C. over a 20 minute period. The toluene phase was separated and analyzed by vapor phase chromatograph with internal standard. Based on the analysis, yields were calculated as 55 percent yield of ethyl 1,4-dimethyl-3-ethoxycarbonylpyrrole-2-acetate, 2 percent yield of methyl 1,4-dimethyl-3-ethoxycarbonylpyrrole-2-acetamide and 4 percent yield of ethyl 1,5-dimethyl-3-ethoxycarbonylpyrrole-2-acetate.

In a comparative example anhydrous gaseous methylamine was bubbled through a mixture of diethyl acetone dicarboxylate and chloroacetone in methylene chloride for about five minutes while the temperature rose from 25 to about 40° C. After reaction for one-half hour, water was added and the reaction mixture was heated to 90° C. for about one-half hour. Extraction with chloroform gave a dark oil containing 23 percent yield of the desired ethyl 1,4-dimethyl-3-ethoxycarbonylpyrrole-2-acetate.

It is thus clear that both an added co-solvent and water are required for the advantageous characteristics of the present invention. Further, other solvents as mentioned hereinabove can be used with advantageous results. Thus, benzene and xylene can also be employed in a manner similar to toluene and with similar results.

The Carson patents, U.S. Pat. Nos. 3,752,826 and 3,865,840, are hereby incorporated by reference as if fully set forth.

Having disclosed the process of the present invention, one skilled in the art can readily envision variations, modifications and changes within the scope and spirit of this invention. Therefore, it is desired that the present invention be limited only by the lawful scope of the following claims.

What is claimed is:

1. In a process for the preparation of a loweralkyl 1,4-diloweralkyl-3-loweralkoxycarbonyl-pyrrole-2-acetate of the formula:

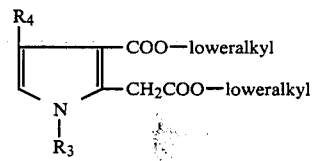

by reacting a mixture of a chloromethyl loweralkyl ketone of the formula: Cl—CH$_2$—CO—R$_4$, with a diloweralkyl acetone dicarboxylate of the formula:

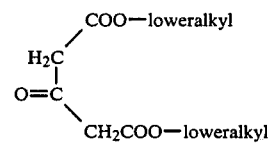

and an aqueous solution of a loweralkylamine of the formula: R$_3$NH$_2$, wherein the foregoing formulas said R$_3$ and said R$_4$ represent loweralkyl, the improvement comprising said reacting being carried out in the presence of an added co-solvent in which said diloweralkyl acetone dicarboxylate is soluble and which can extract said loweralkylamine from the aqueous phase at a rate so that the exothermic reaction is moderated and the product remains in solution, said co-solvent being an aromatic hydrocarbon compound having a boiling point in the range of from about 75° to 150° C.

2. The improved process of claim 1 wherein said co-solvent is selected from the group consisting of benzene, toluene and xylene.

3. The improved process of claim 1 wherein said cosolvent is toluene.

4. In a process for the preparation of a loweralkyl 1,4-diloweralkyl-3-loweralkoxycarbonyl-pyrrole-2-acetate of the formula:

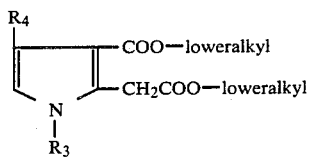

by reacting a mixture of a chloromethyl loweralkyl ketone of the formula: $Cl-CH_2-CO-R_4$, with a diloweralkyl acetone dicarboxylate of the formula:

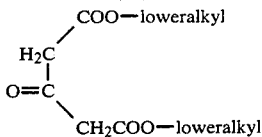

and an aqueous solution of a loweralkylamine of the formula: $R_3NH_2$, where in the foregoing formulas said $R_3$ and said $R_4$ represent loweralkyl, the improvement comprising said reacting being carried out in the presence of an added co-solvent which is an aromatic hydrocarbon compound having a boiling point in the range of from about 75° to about 150° C.

* * * * *